United States Patent [19]

Smith

[11] Patent Number: 5,007,931

[45] Date of Patent: Apr. 16, 1991

[54] POROUS COATED PROSTHESIS

[75] Inventor: Todd S. Smith, Warsaw, Ind.

[73] Assignee: Boehringer Mannheim Corporation, Indianapolis, Ind.

[21] Appl. No.: 518,943

[22] Filed: May 4, 1990

[51] Int. Cl.$^5$ .......................... A61F 2/32; A61F 2/28
[52] U.S. Cl. ........................................ 623/23; 623/16
[58] Field of Search .................................... 623/22, 23

[56] References Cited

U.S. PATENT DOCUMENTS

| | | | |
|---|---|---|---|
| 3,605,123 | 9/1971 | Hahn | 3/1 |
| 3,740,769 | 6/1973 | Haboush | 3/1 |
| 3,855,638 | 12/1974 | Pilliar | 3/1 |
| 4,195,367 | 4/1980 | Kraus | 3/1.91 |
| 4,536,894 | 8/1985 | Galante et al. | 623/22 |
| 4,546,501 | 10/1985 | Gustilo et al. | 623/23 |
| 4,681,589 | 7/1987 | Tronzo | 623/22 |
| 4,718,915 | 1/1988 | Epinette | 623/23 |
| 4,743,262 | 5/1988 | Tronzo | 623/16 |
| 4,840,632 | 6/1989 | Kampner | 623/22 |
| 4,854,496 | 8/1989 | Bugle | 228/193 |
| 4,865,608 | 9/1989 | Brooker, Jr. | 623/23 |
| 4,944,759 | 7/1990 | Mallory et al. | 623/22 |

Primary Examiner—David J. Isabella
Assistant Examiner—Trinh Nguyen
Attorney, Agent, or Firm—Albert W. Hilburger

[57] ABSTRACT

An artificial implant includes an elongated stem member which is intended for cementless fixation in the medullary canal of a long bone. The stem member is provided with one or more longitudinally extending channels. A porous medium for enabling and encouraging bone ingrowth fixation is bonded to the bottom surface of each channel but is free of the sidewalls of the channel. It has a first outer surface lying in a plane generally parallel to that of the external surface of the stem member and second and third surfaces lying generally, respectively, in angularly spaced radial planes containing the longitudinal axis of the stem member. The resulting implant has a flexibility which can be tailored to that of the bone. Also, the porous medium enables an initial interference fit with the medullary canal of the long bone as well as bone ingrowth fixation over a substantially enlarged surface area than previously possible. Also, notching the high stress region on the external surface of the stem member as previously caused by application of the porous medium to the outermost, external, surface of the stem member is avoided.

7 Claims, 1 Drawing Sheet

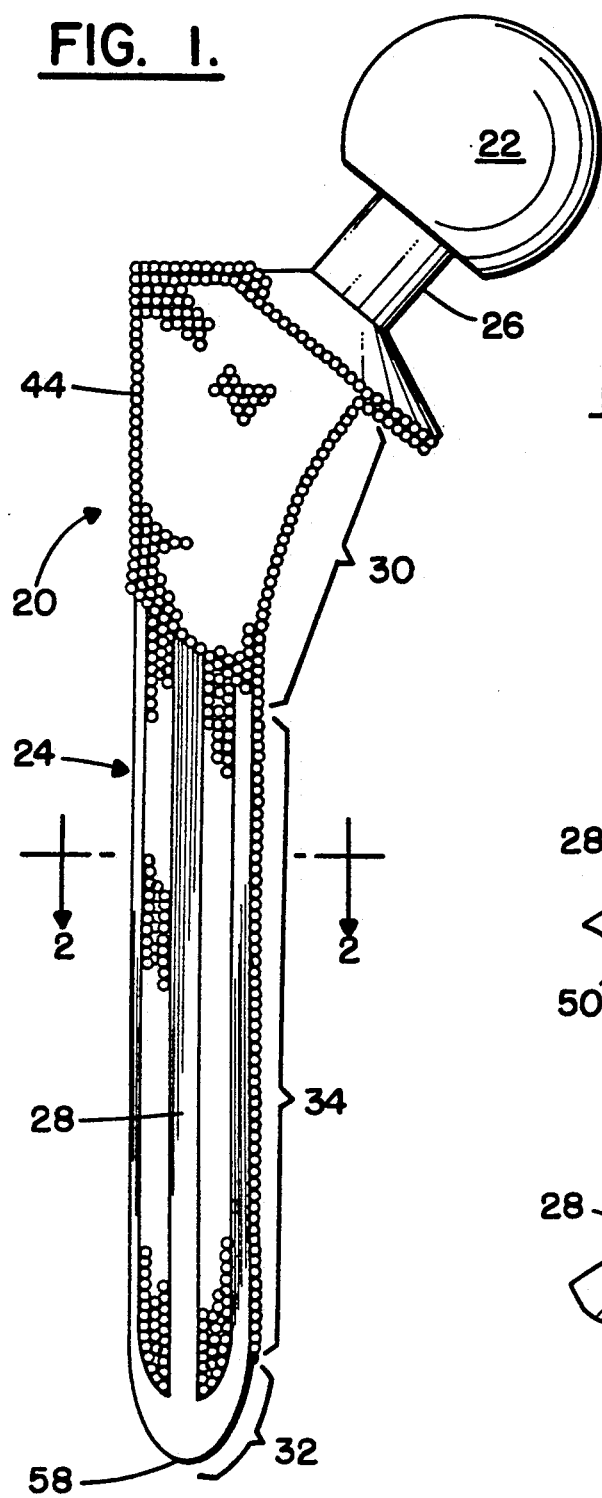
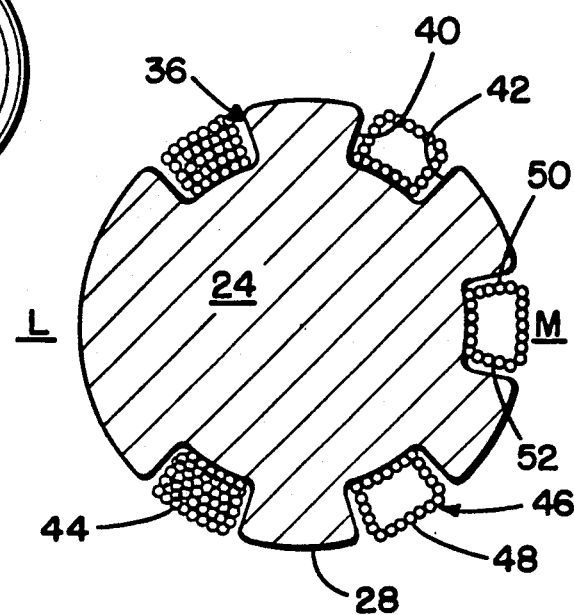
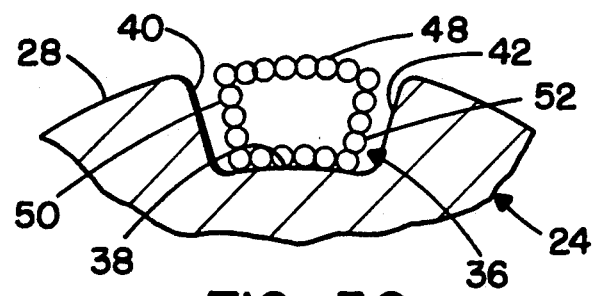
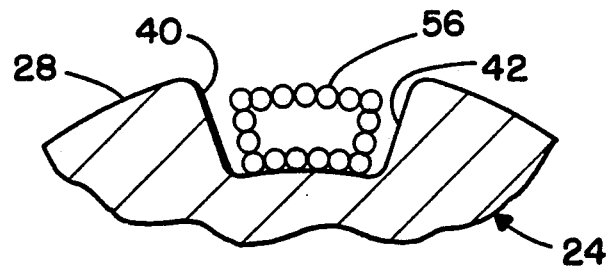
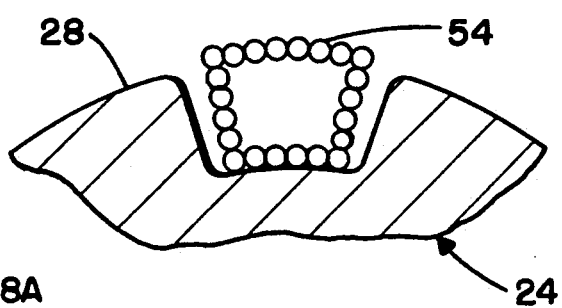
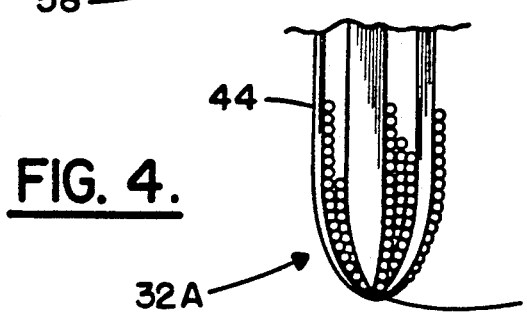

POROUS COATED PROSTHESIS

BACKGROUND OF THE INVENTION

1. Field of the Invention

The present invention relates generally to prosthetic devices for replacing injured or diseased natural members and, more particularly, to such devices provided with porous surfaces for promoting bone ingrowth fixation.

Although the invention need not be so limited, it is disclosed in relation to a hip prosthesis adapted for insertion into the upper medullary canal in the femur of a patient. The hip prosthesis of this invention is of the type generally characterized as including a head or ball member, a shaft or stem member for insertion into the intramedullary canal, and a neck member connecting the head and stem. The prosthesis also includes at least one porous metal surface portion which provides for stabilization by bone ingrowth fixation without requiring any cement.

2. Description of the Prior Art

Hip prostheses are known in the art and these have included various design configurations of the various components, including the head member, neck, collar and stem. In recent years, prosthetic devices have been provided with porous surfaces for bone ingrowth fixation. An excellent example of such a surface results from application of the proprietary porous metal coating of DePuy Division of Boehringer Mannheim Corporation provided under the trademark "POROCOAT". Representative of patents in this field include U.S. Pat. Nos. 3,605,123 to Hahn, No. 3,855,638 to Pilliar, No. 4,536,894 to Galante et al, and No. 4,854,496 to Bugle.

By providing a bone ingrowth surface on the prosthetic device, a stable fixation can be achieved without the use of bone cement. However, even with prosthetic devices provided with a bone ingrowth fixation surface or surfaces, sufficient bone ingrowth fixation to provide long term stabilization requires that the prosthesis be stably fixed without movement for a period of time post implantation, and any excessive relative motion between the bone and the prosthesis during that period can prevent or compromise such fixation. This is a particularly significant problem in view of the difficulty of fitting the prosthesis with sufficiently close tolerances to provide large contact areas between the porous material and the bone, even where the entire outer surface of the prosthesis is fabricated from porous material.

It is generally understood that the success of a cementless joint implant arthroplasty depends upon the initial stability of the implant following its insertion into the skeletal member. The stability of the implant is, in turn, determined essentially by two factors: (1) the geometry or shape of the implant and (2) the surface roughness of the implant. Regarding the latter, it is desirable to porous coat all of the implant surface which is in apposition with the bone. Essentially, the increased surface area provided by the porous coating results in an exceedingly strong friction fit between stem and bone which promotes implant stability improving the likelihood of bone ingrowth fixation for long term fixation. The stability of the implant may be even further enhanced by providing an interference fit between the outer surface of the porous coating and the bone by allowing the porous coated region to protrude beyond the boundary formed by the smooth outer surface of the implant.

It is a known phenomenon, though, that the porous coating can act as a notch, that is, a surface defect on the surface of the implant. Certain preferred materials for prostheses such as the titanium alloy Ti-6Al-4V are "notch sensitive" and can experience a drastic reduction in fatigue strength when the porous coating is located in high stress regions of the implant. Typically, the fatigue strength of titanium alloys can be reduced by approximately 70% when porous coated.

Also, it has been postulated with some degree of clinical support that stemmed implants with very thick sections and a resultant high bending stiffness may have a deleterious effect on the viability of the bone into which it is placed. The stiff stem, in effect, stress protects the surrounding bone. If bone is not regularly stressed to within certain limits the bone will atrophy until the stress level rises to a value within the desired range. In the case of the thickest and stiffest stems the amount of atrophy can be severe. This phenomenon and other approaches for addressing the problem have been disclosed in U.S. Pat. No. 4,808,186 and in U.S. application Ser. No. 391,660 filed Aug. 8, 1989.

The purposes of the present invention are three-fold. A first purpose is to reduce the section modulus and resulting bending stiffness of thick stems to reduce the amount of bone stress protection. A second purpose is to porous coat significant surface areas of the stem in such as way as to avoid notching the high stress regions yet still provide for a tight friction, even interference, fit of the stem within the intramedullary canal. A third purpose is to obtain a maximum surface area for the porous coating to thereby obtain the strongest possible bond between the bone and the prosthesis.

When a femoral hip implant is loaded, the stem is typically placed in a bending mode of stress. In the bending mode of loading the highest stresses exist on the most lateral outer fibers of the stem. The stresses decrease to zero in a linear fashion toward the center or longitudinal axis of the stem which is therefore referred to as the neutral axis. A porous coating located at the outer fiber high stress region would unfortunately operate to notch the implant substrate and can likely lead to premature failure. According to the invention, however, channels are cut into the stem in a longitudinal direction. The porous coating is attached to the bottom of the channels only. In this manner, the fiber stresses are lower to an extent primarily dependent upon the depth of the channel. Notching the high stress region is thereby avoided. The porous coating can be built up to a thickness to be generally level with the outer surface of the implant. Therefore, a portion of the desired friction fit in the stem region of an implant can be achieved.

The longitudinal channels also serve to reduce the section modulus of the stem yielding it more flexible. This maintains the viability of the bone in the stem region by reducing the amount of stress protection usually caused by large solid stems.

Still another benefit of the invention resides in the significantly increased surface area thereby provided by the porous coating for enhanced bone ingrowth fixation. That is, the porous coating applied in the manner of the invention does not only present its usual outer surface lying generally within or parallel to an outer surface of the stem. It also presents two additional surfaces which lie in radial planes generally parallel to but spaced from the sidewalls of the channel.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms. Like numerals refer to like parts throughout the disclosure.

BRIEF DESCRIPTION OF THE DRAWINGS

FIG. 1 is a side elevation view illustrating a femoral component for a hip prosthesis which embodies the invention;

FIG. 2 is a cross section view taken generally along line 2—2 in FIG. 1;

FIGS. 3A, 3B, and 3C are detail cross section views, enlarged, of a portion of FIG. 2 depicting, respectively, a porous medium particularly receptive to bone ingrowth fixation having different thicknesses; and FIG. 4 is an enlarged detail side elevation view illustrating a modified distal end of the femoral component illustrated in FIG. 1.

DETAILED DESCRIPTION OF THE PREFERRED EMBODIMENTS

Turn now to the drawings and, initially, to FIGS. 1 and 2 which generally illustrate, by the way of example, a femoral component 20 which embodies the invention. It was previously explained that the invention can be applied to a variety of stemmed implants and need not be restricted to a femoral implant. In any event, the femoral component 20 is illustrated as having a head member 22 for rotatable engagement with an acetabular component (not shown), an elongated stem member 24, and a neck member 26 integrally joining the head member and the stem member. In a customary fashion, the stem member 24 has a longitudinal axis and an external surface 28 and is intended for cementless fixation in the intramedullary canal of a femur (not shown).

As illustrated in FIG. 1, the stem member 24 extends generally between a proximal portion 30 adjacent the neck member 26 and a distal portion 32 which is distant from the neck member. An intermediate portion 34 of the stem member 24 is illustrated in FIGS. 1 and 2 as having a plurality of longitudinally extending channels 36 at circumferentially spaced locations. The channels 36 are defined by a bottom surface 38 and opposed sidewalls 40, 42. The depth and width of the channels 36 may be of any dimensions suitable for a particular implant. The bottom surface 38 may be planar, or may be curved, conforming generally to the surface of an imaginary cylinder whose axis is the longitudinal axis of the stem member 24 and having a radius reaching to the bottom surface 38. In a similar manner, the sidewalls 40, 42 may lie in angularly spaced radial planes which contain the longitudinal axis of the stem member 24. In order to avoid stress concentrations, it is desirable that the interface between the external surface 28 and the sidewalls 40, 42 be rounded and, similarly, the interface between the sidewalls and the bottom surface 38. Such a construction assures a smooth blending of the adjoining surfaces rather than sharp lines of demarcation which would give rise, adversely, to localities subject to unduly high stresses.

With particular attention to FIG. 2, it will be noted that the channels 36 are more prominent on the medial side of the stem member 24, denoted by the letter M, which is subject to compressive stresses than on the lateral side, denoted by the letter L, which is subject to maximum tensile stresses in the fibers of the external surface 28. This construction serves to avoid any possibility of notching external surface 28 during the forming of the channels 36 in the stem member 24 and, subsequently, when the porous coating is applied.

As seen in FIG. 1, it is desirable to provide a porous medium or coating 44 on the proximal portion 30 of the stem member 24. While the proximal portion 30 is the most massive part of the stem member 24, it is also received in the most massive part of the bone and is not subjected to stresses of the magnitude imparted to the intermediate portion 34. As a result, it is acceptable for its entire surface to be provided with the porous medium 44 without the benefit of channels 36.

However, because of the increased and cyclic stresses to which the intermediate portion 34 is subjected, the porous medium 44 is provided only within the regions of the channels 36 and not on the external surfaces 28. Further in keeping with the invention, the porous medium 44, which may be, for example, the proprietary coating of DePuy Division of Boehringer Mannheim Corporation provided under the trademark "POROCOAT", is suitably bonded to the bottom surface 38 of each channel 36 while remaining free of the sidewalls 40, 42. The porous medium, which serves to permit and encourage bone ingrowth fixation, thereby presents an outer surface 46 which is more specifically defined by a first surface 48 which lies in a plane generally parallel to a plane of the external surface 28, together with second and third surfaces 50, 52, respectively, which lie generally in angularly spaced radial planes which contain the longitudinal axis of the stem member 24.

As seen particularly well in FIGS. 2 and 3A, 3B, and 3C, the second surface 50 is spaced from the sidewall 40 and the third surface 52 is spaced from the sidewall 42. While the first surface 48 may lie in a plane of the external surface 28 (FIG. 3A), it may lie in a plane 54 (FIG. 3B) which lies beyond the plane of the external surface 28 in a direction away from the longitudinal axis of the stem member 24. By so doing, an interference fit between the stem member 24 and the bone would occur during implantation, substantially improving implant stability from the very moment of implantation into the bone. In certain other instances it may be desirable for the first surface 48 to assume a plane nearer to the longitudinal axis of the stem member 24 than the external surface 28, witness plane 56 shown in FIG. 3C. This may occur, for example, in a situation in which the underlying bone is brittle such that it would not be desirable to further stress the bone or, in revision surgery, when it would not serve any particular advantage.

FIG. 4 illustrates another embodiment of the invention. Specifically, a distal portion 32A is modified such that channels 36 are provided down to its tip end 58A with the porous medium 44 present therein in the manner previously described. Such a construction would thereby enhance bone growth over all surfaces of the stem member 24 and, as a result, further improve the probability of success for a long term fixation.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A femoral component for a hip prosthesis comprising:
    a head member for rotatable engagement with an acetabular component;
    an elongated stem member having a longitudinal axis and an external surface and intended for cementless fixation in the intramedullary canal of a femur; and
    a neck member integrally joining said head member and said stem member;
    said stem member extending between a proximal portion adjacent said neck member and a distal portion distal from said neck member, and including an intermediate portion between and integral with said proximal portion and said distal portion, said intermediate portion having a plurality of longitudinally extending channels, each of said channels defined by a bottom surface and opposed sidewalls connecting said bottom surface to said external surface; and
    a porous medium for encouraging bone ingrowth fixation bonded to said bottom surface of each of said channels while remaining free of said sidewalls, said porous medium presenting an outer surface generally defined by a first surface lying in a plane generally parallel to a plane of said external surface and second and third surfaces lying generally, respectively, in angularly spaced radial planes containing said longitudinal axis.

2. A femoral component as set forth in claim 1 wherein said porous medium substantially covers said external surface of said proximal portion.

3. A femoral component as set forth in claim 1 wherein said distal portion has a plurality of longitudinally extending channels communicating with an associated one of said channels in said intermediate portion, each of said distal channels defined by a bottom surface and opposed sidewalls connecting said bottom surface to said external surface; and
wherein said porous medium is bonded to said bottom surface of each of said distal channels while remaining free of said sidewalls thereof, said porous medium in said distal channels presenting an outer surface generally defined by a first surface lying in a plane generally parallel to a plane of said external surface and second and third surfaces lying generally, respectively, in angularly spaced radial planes containing said longitudinal axis.

4. A femoral component as set forth in claim 1 wherein the plane of said first surface lies beyond the plane of said external surface in a direction away from said longitudinal axis.

5. An artificial implant comprising:
    an elongated stem member having a longitudinal axis and an external surface and intended for cementless fixation in the medullary canal of a long bone, said stem member having at least one longitudinally extending channel defined by a bottom surface and opposed sidewalls connecting said bottom surface to said external surface; and
    a porous medium for encouraging bone ingrowth fixation bonded to said bottom surface, said porous medium having a first outer surface lying in a plane generally parallel to a plane of said external surface and second and third surfaces lying generally, respectively, in angularly spaced radial planes containing said longitudinal axis.

6. A femoral component as set forth in claim 5 wherein the plane of said first surface lies beyond the plane of said external surface in a direction away from said longitudinal axis.

7. A femoral component for a hip joint prosthesis comprising:
    an elongated stem intended for implantation in the intramedullary canal of a femur having a longitudinal axis and including a proximal member nearest the hip joint, a distal member distant from the hip joint, and an intermediate member connecting said proximal member and said distal member, said intermediate member having an outer surface and a plurality of longitudinally extending channels at spaced circumferential locations about said intermediate member, each of said channels having a bottom surface and sidewalls blending smoothly with said bottom surface and with said outer surface; and
    a porous medium for encouraging bone ingrowth fixation bonded to said bottom surface of each of said channels while remaining free of said sidewalls, said porous medium presenting an outer surface generally defined by a first surface lying in a plane generally parallel to a plane of said external surface and second and third surfaces lying generally, respectively, in angularly spaced radical planes containing said longitudinal axis.

* * * * *